United States Patent [19]

Burrows

[11] Patent Number: 5,617,871
[45] Date of Patent: Apr. 8, 1997

[54] SPREAD SPECTRUM TELEMETRY OF PHYSIOLOGICAL SIGNALS

[75] Inventor: Fremont W. Burrows, Woodinville, Wash.

[73] Assignee: Quinton Instrument Company, Bothell, Wash.

[21] Appl. No.: 347,750

[22] Filed: Dec. 1, 1994

Related U.S. Application Data

[63] Continuation of Ser. No. 146,260, Nov. 2, 1993, Pat. No. 5,381,798.

[51] Int. Cl.$^6$ .................................................. A61B 5/0402
[52] U.S. Cl. ............................ 128/696; 128/903; 607/32; 607/60
[58] Field of Search .................................... 128/630, 696, 128/903; 607/32, 60

[56] References Cited

U.S. PATENT DOCUMENTS

| | | | |
|---|---|---|---|
| 3,409,007 | 11/1968 | Fuller | 128/2.06 |
| 3,606,881 | 9/1971 | Woodson | 128/2.06 E |
| 3,727,190 | 4/1973 | Vogelman et al. | 340/172.5 |
| 3,810,102 | 5/1974 | Parks, III et al. | 340/172.5 |
| 3,882,853 | 5/1975 | Gofman et al. | 128/2.06 E |
| 3,927,663 | 12/1975 | Russell et al. | 128/2.06 A |
| 3,970,996 | 7/1976 | Yasaka et al. | 340/172.5 |
| 3,972,320 | 8/1976 | Kalman | 128/2.1 A |
| 3,989,036 | 11/1976 | Sasamori | 128/2.06 E |
| 3,998,213 | 12/1976 | Price | 128/2.1 B |
| 4,173,971 | 11/1979 | Karz | 128/702 |
| 4,177,817 | 12/1979 | Bevilacqua | 128/802 |
| 4,216,462 | 8/1980 | McGrath et al. | 340/150 |
| 4,365,634 | 12/1982 | Bare et al. | 128/640 |
| 4,381,012 | 4/1983 | Russek | 128/644 |
| 4,475,208 | 10/1984 | Ricketts | 375/1 |
| 4,494,551 | 1/1985 | Little, III et al. | 128/696 |
| 4,494,552 | 1/1985 | Heath | 128/696 |
| 4,515,162 | 5/1985 | Yamamoto et al. | 128/640 |
| 4,531,527 | 7/1985 | Reinhold, Jr. et al. | 128/696 |
| 4,724,435 | 2/1988 | Moses et al. | 340/870.13 |
| 4,763,660 | 8/1988 | Kroll et al. | 128/640 |
| 4,784,162 | 11/1988 | Ricks et al. | 128/903 |
| 4,803,625 | 2/1989 | Fu et al. | 364/413.03 |

(List continued on next page.)

FOREIGN PATENT DOCUMENTS 339471  11/1989  European Pat. Off. .

OTHER PUBLICATIONS

J. Swanberg, "Spread–Spectrum UHF Encrypted–Command Patient Link," IEEE Engineering in Medicine & Biology Society 11th Annual International Conference, Nov. 9–12, 1989, 1391–1392 (4 pages).

Author unknown, "Sound Reasons for Radio–wave Links," HealthWeek, Sep. 23, 1991, p. 41 (2 pages).

Medical Data Electronics, "Escort–Link Central Station Model E3200B" Product Brochure, Jun. 1994 (2 pages).

G. J. Newton et al., "Use of Spread Spectrum Radio Technology for Networking Health Physics Instruments," Health Physics Society 36th Annual Meeting, Jul. 21–26, 1991, Abstracts of Papers Presented, TPM–A6, S30 (2 pages).

Proxim, "Spread Spectrum OEM RF Modem" Product Brochure, Jun. 1991 (2 pages) and accompanying letter from sales representative Robert Kroskrity, Apr. 2, 1992.

Proxim, "ProxLink™ Radio Module" Product Brochure, Oct. 1991 (2 pages).

R. C. Dixon, *Spread Spectrum Systems* (2nd ed. 1984), Preface, pp. v–vii and ix.

R.C. Dixon, *Spread Spectrum Systems* (2nd ed. 1984), Chapter 1, pp. 1–13.

*Primary Examiner*—William E. Kamm
*Attorney, Agent, or Firm*—Montgomery W. Smith; Andrew J. Beck; Richard D. Allison

[57] ABSTRACT

A system for the transmission of physiological signals from a patient to a display analysis and/or recording device using a spread spectrum transmission technique to reduce interference with the detection of the transmitted physiological signal wherein multiple channels of the physiological signals are transmitted over a bandwidth of approximately 3 MHz.

24 Claims, 9 Drawing Sheets

U.S. PATENT DOCUMENTS

| | | | |
|---|---|---|---|
| 4,827,943 | 5/1989 | Bornn et al. | 128/668 |
| 4,834,105 | 5/1989 | Matthews et al. | 128/648 |
| 4,835,372 | 5/1989 | Gombrich et al. | 235/375 |
| 4,839,806 | 6/1989 | Goldfischer et al. | 364/413.02 |
| 4,850,009 | 7/1989 | Zook et al. | 379/96 |
| 4,858,615 | 8/1989 | Meinema | 128/668 |
| 4,860,758 | 8/1989 | Yanagawa et al. | 128/662.06 |
| 4,868,863 | 9/1989 | Hartley et al. | 379/98 |
| 4,889,131 | 12/1989 | Salem et al. | 128/671 |
| 4,889,132 | 12/1989 | Hutcheson et al. | 128/680 |
| 4,909,260 | 3/1990 | Salem et al. | 128/721 |
| 4,911,169 | 3/1990 | Ferrari | 128/641 |
| 4,916,441 | 4/1990 | Gombrich | 340/712 |
| 4,952,928 | 8/1990 | Carroll et al. | 340/825.54 |
| 4,955,381 | 9/1990 | Way et al. | 128/640 |
| 4,958,645 | 9/1990 | Cadell et al. | 128/903 |
| 4,966,154 | 10/1990 | Cooper et al. | 128/671 |
| 4,993,421 | 2/1991 | Thornton | 128/670 |
| 4,995,398 | 2/1991 | Turnidge | 128/668 |
| 5,002,064 | 3/1991 | Allain et al. | 128/710 |
| 5,022,404 | 6/1991 | Hafner | 128/696 |
| 5,025,452 | 6/1991 | Sohner et al. | 375/1 |
| 5,036,462 | 7/1991 | Kaufman et al. | 364/413.01 |
| 5,036,856 | 8/1991 | Thornton | 128/670 |
| 5,036,869 | 8/1991 | Inahara | 128/903 |
| 5,050,612 | 9/1991 | Matsumura | 128/670 |
| 5,065,425 | 11/1991 | Lecomte et al. | 379/93 |
| 5,072,383 | 12/1991 | Brimm et al. | 364/413.02 |
| 5,077,753 | 12/1991 | Grau, Jr. et al. | 375/1 |
| 5,166,952 | 11/1992 | Omurg et al. | 375/1 |
| 5,171,977 | 12/1992 | Morrison | 235/375 |
| 5,179,569 | 1/1993 | Sawyer | 375/1 |
| 5,179,571 | 1/1993 | Schilling | 375/1 |
| 5,205,294 | 4/1993 | Flach et al. | 128/696 |
| 5,212,715 | 5/1993 | Pickert et al. | 375/114 |
| 5,333,617 | 8/1994 | Hafner | 128/697 |
| 5,348,008 | 9/1994 | Bornn et al. | 128/903 |

SPREAD SPECTRUM TELEMETRY OF PHYSIOLOGICAL SIGNALS

This is a continuation of application Ser. No. 08/146,260, filed on Nov. 2, 1993, now U.S. Pat. No. 5,381,798.

FIELD OF THE INVENTION

This present invention relates to the field of telemetry used in biomedical applications and more specifically to telemetry of biomedical data using spread spectrum transmission.

DESCRIPTION OF THE PRIOR ART

Telemetry systems that transmit a plurality of patient physiological signals, such as ECG signals, is known. For example, in intensive care units, it is known to use a transmitter located at the patient's bedside to transmit physiological signals from the patient to a central nurses' station which monitors the signals from a plurality of patient transmitters through a multiplexing unit. Nearly any physiological signal such as cardiac or ECG signals, blood pressure, respiration rates, pulse rates and other vital signs are typically monitored and transmitted to the nurses' station. Therefore, multiple patients may be monitored at the nurses' station, and software driven alarms may be used to alert the nurse when one or more of the monitored signals is outside the desired parameters. Other systems allow for the ambulation of the patient so that the signals are transmitted from a unit worn by the patient to a central monitoring unit such as a nurses' station.

Early telemetry systems used FM/FM analog modulation. The analog data which is transmitted in these systems is often susceptible to a large amount of DC drift which is transmitted as true data. The DC drift increases the likelihood of false alarms. Additionally, FM/FM analog modulation systems are not very efficient in their use of the available bandwidth. This limits the number of channels that can be transmitted and the frequency responses of the transmitted channels. Therefore, compromises need to be made in the signal fidelity available in multi-channel FM/FM analog modulation systems.

In more recent telemetry systems, a variety of digital modulation schemes are used to modulate the RF carrier. Examples of digital modulation schemes of this type are frequency shift keying and phase shift keying schemes which use phase lock demodulation. One example of a currently available digital data transmission system is disclosed in U.S. Pat. No. 5,205,294 granted to Flach et al. Although the digital modulation types of systems make better use of the carrier bandwidth than analog transmission systems, their ability to transmit data is still very limited and susceptible to various types of interference. For example, depending on the bit patterns of the system, the data may have intervals of high density ones or zeros which may be transmitted as DC drift in these types of systems. As illustrated by the Flach et al. patent, the emphasis in the development of more recent telemetry systems is to more efficiently use the relatively narrow bandwidths that are conventionally used to transmit the data. Despite the increased efficiency of the Flach et al. device, there are still limited signals that may be transmitted due to the channel and bandwidth limitations of these systems.

As described more fully below, the present invention is directed to a device which uses spread spectrum technology to transmit the physiological data from the patient to the monitoring station. Examples of spread spectrum signaling methods which may be used as part of the present invention are direct sequence modulated systems, frequency hopping systems such as pulsed FM systems or "chirp" modulated systems. One example of a radio communication system which uses a spread spectrum transmission technique of the type used in the present invention is disclosed in U.S. Pat. No. 5,077,753 granted to Grau et al. The use of a spread spectrum system allows for the transmission of more physiological signals while reducing the likelihood of interference or noise.

The present invention is particularly desirable for use with a resting or stress testing ECG system. In current resting or stress testing systems the patient is tethered to the monitoring equipment by a patient cable system or a cable mounted preamp. One of the problems that arises with many patient cable systems is that movement of the cable causes noise or interference in the desired signals. One approach to overcoming the problem of noise or interference with the patient cable system has been to use special cable materials such as conductive plastic shields which are expensive. The length of the cable between the patient and the monitoring equipment in these systems is also limited by the weight of the cable as well as the physical capacitance of the cable so that the length of the cable is typically limited to 10 or 20 feet. Although the weight of the cable may be reduced by using smaller diameter wires, the durability of the cable is then reduced, and the likelihood that noise will be created due to cable movement is similarly increased.

An approach to solving many of the problems described above is to use a cable mounted preamp. The use of the cable mounted preamp solves the problem of noise and allows the length of the wires between the preamp and monitoring unit to be increased. By isolating the physiological signals of the patient at the preamp, the difficulties associated with cable capacitance are substantially eliminated, and digital data may be sent through a smaller diameter cable from the cable mounted preamp to the monitoring unit so that fewer and less complex wires may be used from the preamp. Although the cable mounted preamp solves many of the problems associated with prior resting and stress testing ECG systems, it is still necessary that the patient be tethered to the monitoring unit, and there is a likelihood that the patient may become tangled in the cable during the test.

Therefore, a need remains for a telemetry device which reduces the noise or interference present in current telemetry systems, provides for the transmission of a greater number of signals than is available with current systems and which may be used in a variety of physiological signal monitoring systems, such as resting and stress testing ECG systems. Of particular importance is the need to eliminate the bulky cable connection between the patient or cable mounted preamp and the monitoring unit while providing a data-containing signal which is free from extraneous noise or interference.

SUMMARY OF THE INVENTION

An object of the present invention is to provide a telemetry system which uses a wide bandwidth for transmission to significantly reduce the likelihood of noise or interference as compared to currently available physiological signal transmission systems.

Another object of the present invention is to provide a telemetry system which uses a wide bandwidth to transmit an increased number of signals.

Yet another object of the present invention is to provide a physiological signal transmission system which eliminates the need for transmission cables between the patient and the monitoring equipment.

The present invention is directed to a system which receives physiological signals from a patient and then translates the signals into a format which is suitable for transmission using a spread spectrum signal. The data-containing spread spectrum signal is received by a receiver, and the spread spectrum signal is then decoded and reformatted. The reformatted physiological signal is then displayed, recorded, printed, analyzed or otherwise processed.

In a preferred form of the present invention, the system is used to transmit ECG signals from the patient to a display, recording and/or analysis device via spread spectrum signals. In this type of device, the ECG signals are received from the patient and are amplified and digitized by a physiological data acquisition system such as an ECG front-end system. The digital data is oversampled to enable the front-end system to filter and decimate the data to the desired data rate. The data is then serially transmitted from the ECG front-end system to the spread spectrum transmitter. The spread spectrum transmitter then combines the data with a digital code sequence having a bit rate which is much higher than the data signal bit rate. The signal is then transmitted by the spread spectrum transmitter over a wide frequency bandwidth such as a bandwidth of about 3 MHz which is preferably in the 902–928 MHz band.

The spread spectrum signal is then received by the spread spectrum receiver and demodulated to the original serial data stream. A synchronization detector is then used to decode the frame and word synchronization of the serial data stream for use by the reformatting processor. The reformatting processor assembles the words and other data according to the-required formats. The reformatting processor then outputs the words and other data serially with a clock, word synchronizer and digital data signal to the display, recording and/or analysis device.

An advantage of the present invention is that it may be used with nearly any physiological signal to transmit nearly error free signals to a monitoring unit for the display, recording and/or analysis of the desired signal.

Another advantage of the present system is that multiple transmitting units may be used to transmit data to one or more receiving units. Additionally, a single receiving unit may be used to selectively receive data from a plurality of patients.

Yet another advantage of the present invention is that more data may be transmitted in the data stream than with many of the currently available telemetry systems due to the increased data transmission rates.

A further advantage of the present invention is that it preferably uses multiple independent frequency channels and interfaces synchronously and serially at a preferred fixed rate of about 121K bits per second or greater.

Further advantages of the present invention are that the use of spread spectrum transmission for physiological data provides selective addressing capabilities, multiple access with code division multiplexing and increased interference rejection.

DETAILED DESCRIPTION OF THE PREFERRED EMBODIMENTS

Figure 1:
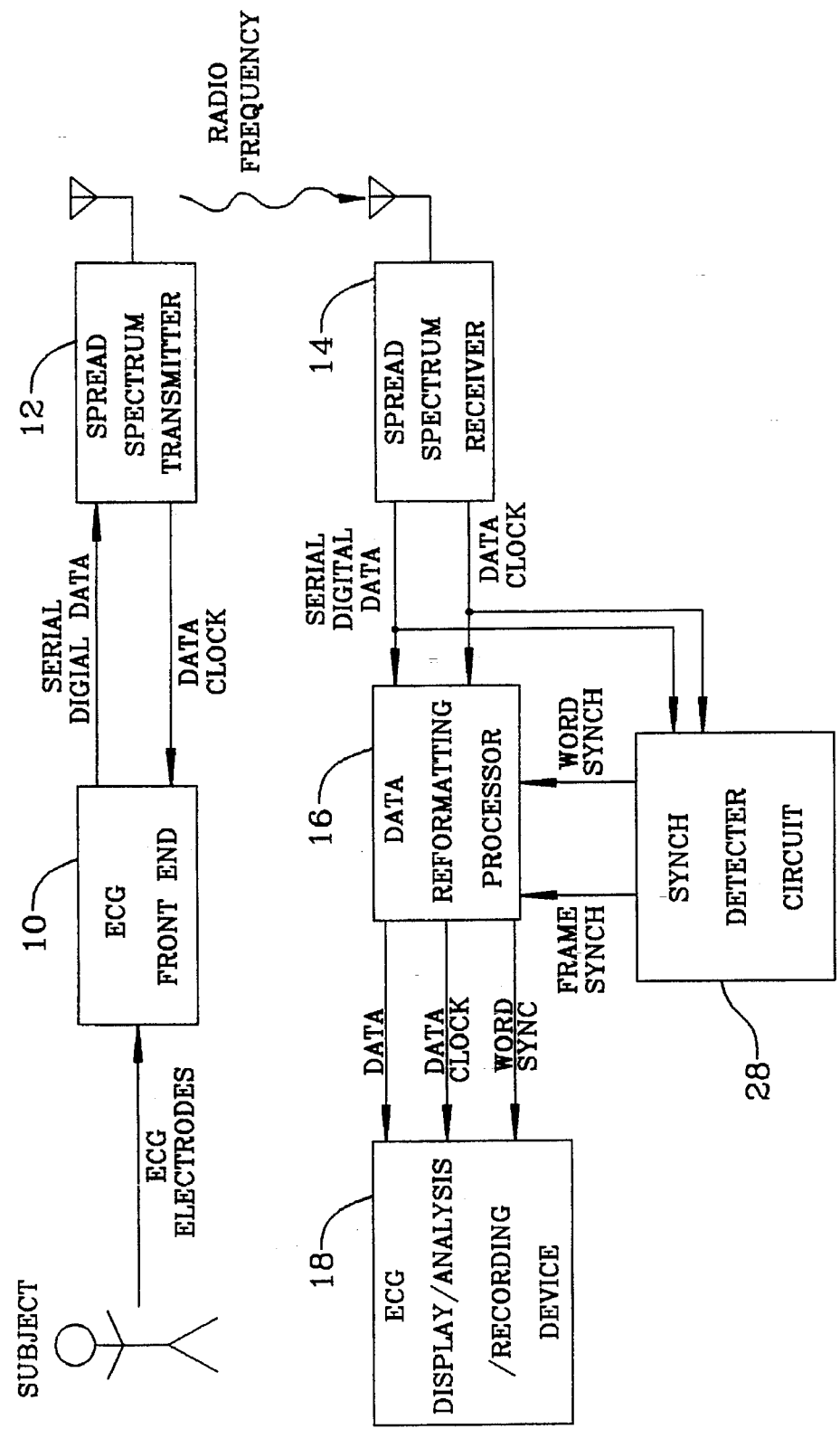
FIG. 1 is a schematic block diagram of the preferred form of the present invention.

FIG. 1 provides a general overview of the preferred form of the present invention for use in the transmission and reception of ECG signals. It should be understood that although the preferred form of the present invention is described below in the context of a resting or stress testing ECG system, various other physiological signals may be transmitted and received either individually or in combination without departing from the scope of the present invention.

As shown in FIG. 1, the physiological signals are received by one or more electrodes or sensors which are located on the patient in a conventional manner. In the preferred embodiment, the electrode signals are combined into conventional lead configurations which are preferably sensed by eight or more data channels which form part of a physiological data acquisition system shown here as an ECG front end 10. The ECG signals are then amplified and digitized by the front end 10 and oversampled to allow the data to be filtered as described more fully below. The data is then decimated so that a preferred data rate of approximately 121K bits per second is achieved. In this embodiment, the data clock signal is received by the front end 10 from the spread spectrum transmitter 12 so that the serial digital data signal from the front end 10 is preferably synchronous. Alternately, the front end 10 may include a clock therein.

The spread spectrum transmitter 12 receives the serial digital data signal from the front end 10 and combines or multiplies the data with a digital code sequence to create the spread spectrum signal. A pseudo random chipping sequence, such as a Barker code, may be used as the digital code to create the spread spectrum signal. The digital code sequence has a bit rate which is much higher than the data signal bit rate, and the transmitter 12 preferably transmits across a bandwidth of about 3 MHz or more in the 902–928 MHz band range although other ranges such as 2400–2483 or 5725–5850 MHz may also be used.

In the preferred embodiment, the data is transmitted via a "direct sequence" modulation system wherein the carrier is modulated by a digital code sequence whose bit rate is much higher than the information signal bit rate. Alternately, other spread spectrum transmission techniques may be used such as frequency hopping wherein the carrier frequency is shifted in a discrete pattern which is dictated by a code sequence or pulsed FM modulation where a carrier is swept over a wide band during a given pulse interval.

The receiver 14 receives the spread spectrum signal from the transmitter 12 and demodulates and despreads the signal into the serial data stream and data clock signal. The serial data stream and clock signal are then received by the data reformatting processor 16 and the synchronization detector circuit 18.

The synchronization detector circuit 18 is preferably a program or a logic state machine that searches the data stream for framing words. Examples of logic devices that are believed to be readily adaptable for use in the present invention are various programmable logic devices or field programmable gate arrays. In the preferred form of this invention, the word synchronizer generates a pulse every 11 bits to frame the serial words of the data stream. The frame and word synchronization is then transmitted to the data reformatting processor 16. Alternately, the receiver may be programmed to search the transmitted data bit by bit to identify framing words or other characteristic bit arrangements.

Figure 3:
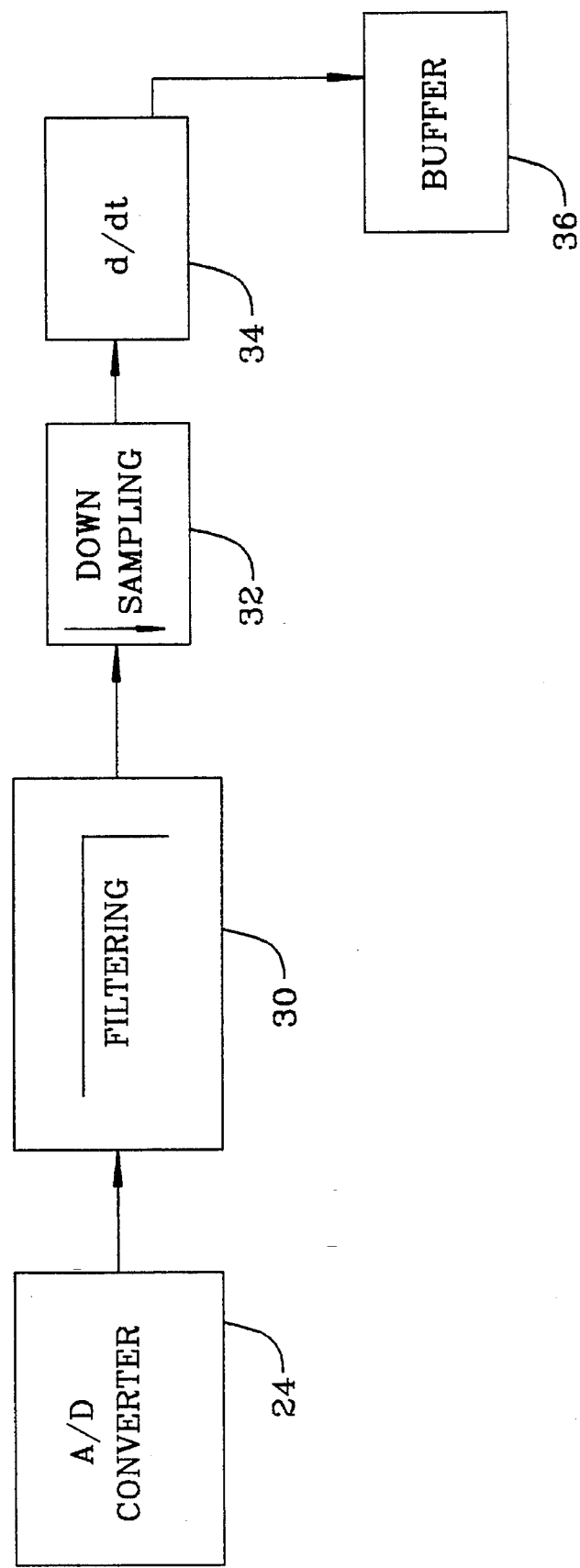
FIG. 3 is a schematic block diagram showing further details of the process used by the digital signal processor of the preferred form of the present invention.
Figure 9:
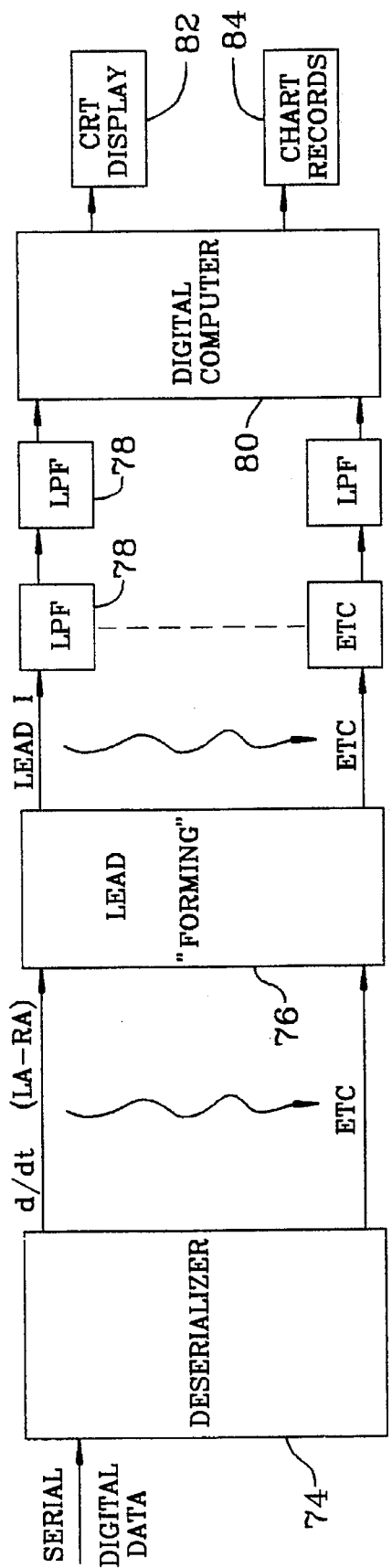
FIG. 9 is a schematic block diagram showing further details of the display, analysis and recording system of the preferred form of the present invention.

The data reformatting processor 16 receives data from the spread spectrum receiver 14 as twenty-two 11-bit words at 121K bits per second and reformats it as output at 128K bits per second. The display, analysis and/or recording system or ECG back end 18 in this embodiment receives the serial digital data stream, a 128K bit per second clock signal and a word synchronization signal from the reformatting processor 16. Because the serial input is a differentiated electrode signal, the back end 18 must reform the ECG lead signals and integrate the data using one or more low pass filters to restore the low frequencies of the original signal. Alternately, if the output of the reformatting processor 16 is to be an analog data stream, the reformatting processor 16 must convert the serial digital data stream into an analog data stream which is then applied to a track and hold system to create signals which are identical to the signals originally received by the front end 10 via the electrodes in systems that do not differentiate the data as shown in FIG. 3. This alternate type of system is shown in FIG. 9 and described more fully below. The analog data stream may then be connected to a conventional ECG display, analysis or recording device, and the ECG device will process the signal as if it were received directly from the patient.

Figure 2:
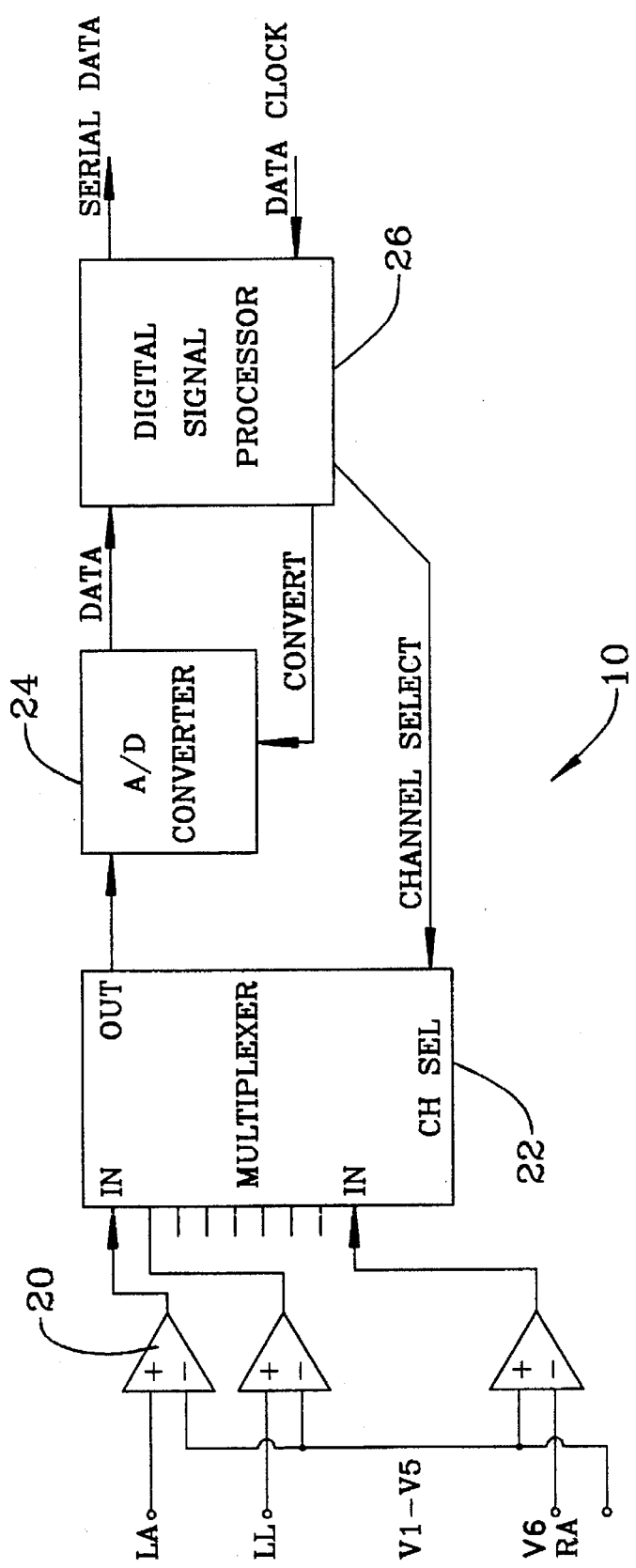
FIG. 2 is a schematic block diagram showing further details of the physiological data acquisition system of the preferred form of the present invention.

As shown in more detail in FIG. 2, the front end 10 receives the physiological signals from the patient and converts them to a serial digital data stream for use by the spread spectrum transmitter 12. In the preferred form of the present invention, the front end 10 includes amplifiers and filter circuits 20 to increase the signal strength and filter out high frequency noise. After the eight channels are differentially amplified, they are fed directly to an analog multiplexer 22. The digital signal processor 26 gates each of the eight channels of ECG lead signals through the multiplexer 22, one at a time. The ECG signal is then compared to an estimate of that signal which is derived from prior measurements. The difference is then digitized by the A to D converter 24 and processed by the digital signal processor 26.

As shown in FIGS. 2 and 3, the digital signal processor 26 controls the channel sequencing of the multiplexer 22, the A to D conversion process and data transmission to the spread spectrum transmitter 12. In the preferred form of the present invention, the digitized data from the A to D converter 24 is received by the digital signal processor 26 as 8-bit words. The multiplexer 22 is controlled by the digital signal processor 26 so that each channel is sampled 8,000 times per second. This means that the A to D converter 24 samples the eight channels of the preferred embodiment 8,000 times per second for a total sampling rate of 64,000 times per second. The effective input rate is then eight bits times 64,000 samples per second or 512,000 bits per second. As shown in FIG. 3 the data for each channel from the A to D converter 24 is filtered 30, downsampled 32, and differentiated 34 and then placed in a buffer 36 by the digital signal processor 26 to form twenty-two 11-bit words at 121K bits per second. The signal is preferably filtered by a low pass filter 30 to perform an anti alias or interpolation and is differentiated 34 to provide digital serial output to the spread spectrum transmitter 12. Although FIG. 2 shows the clock signal being transmitted from the spread spectrum transmitter 12 to the digital signal processor 26, it is anticipated that the digital signal processor 26 or nearly any other element of the front end 10 may contain its own clock signal generator as long as synchronous data is supplied to the spread spectrum transmitter 12.

Figure 4:
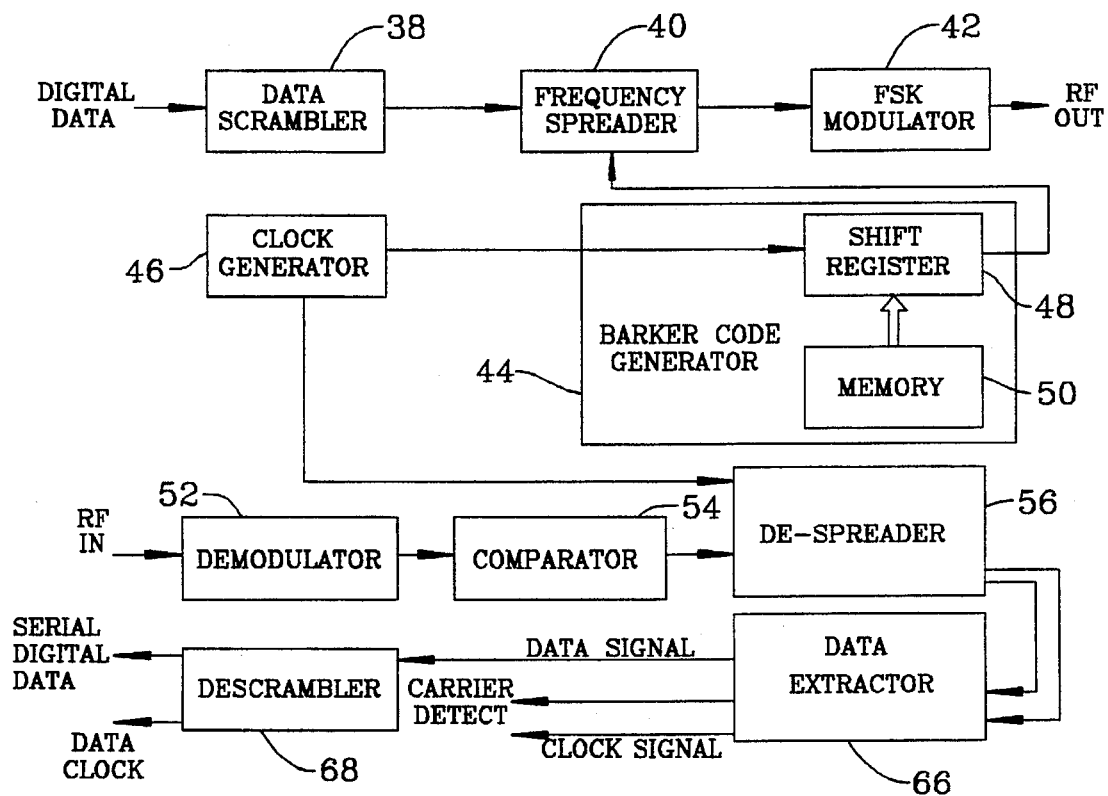
FIG. 4 is a schematic block diagram showing further details of one form of the spread spectrum transmitter and receiver used as part of the preferred form of the present invention.

As shown in FIG. 4, in a preferred form of the spread spectrum transmitter 12, the serial digital data from the digital signal processor 26 is scrambled 38, spread 40 and then used to drive a frequency shift keyed modulator 42. A master clock 46 provides clock signals to the scrambler 38 and the generator 44. The serial digital data is preferably spread by multiplying the modulated signal by a second signal that comprises a spreading signal. Alternately and more preferably, the digital data is preferably combined with a pseudo random chipping sequence to produce the spread spectrum signal which is then transmitted across a bandwidth of about 3 MHz in a predefined frequency band such as 902–928 MHz. The chipping sequence signals are preferably obtained from a generator 44 which is preferably an 11-bit Barker code (i.e., the binary bit sequence 10110111000) or an inverse or reversal thereof. The generator 44 preferably includes a shift register 48 which is parallel loaded from a memory 50 that contains a predetermined chipping sequence. The modulator 42 of this embodiment is driven by the spread spectrum signal to produce a radio frequency (RF) output so that the modulation rate corresponds to the chipping rate.

In the spread spectrum receiver 14, broadcast data is received by a conventional frequency demodulator 52 which converts frequency values to voltage signals. The demodulator output is provided to the digital comparator 54 which compares the voltages to a predetermined threshold value that determines whether a given output of the demodulator should be interpreted as a binary "1" or as a binary "0".

Further, the receiver system in FIG. 4 includes a despreader 56 that employs single bit quantization and oversampling techniques for digitally correlating demodulated signals with a pseudo-random chipping sequence. In practice, the de-spreader 56 uses the same chipping sequence as the transmitter 12 (i.e., the 11-bit Barker code). Also in practice, each chip of the 11-bit Barker code is preferably sampled approximately six times in order to provide a measure of immunity to clock inaccuracies and jitter.

Figure 5:
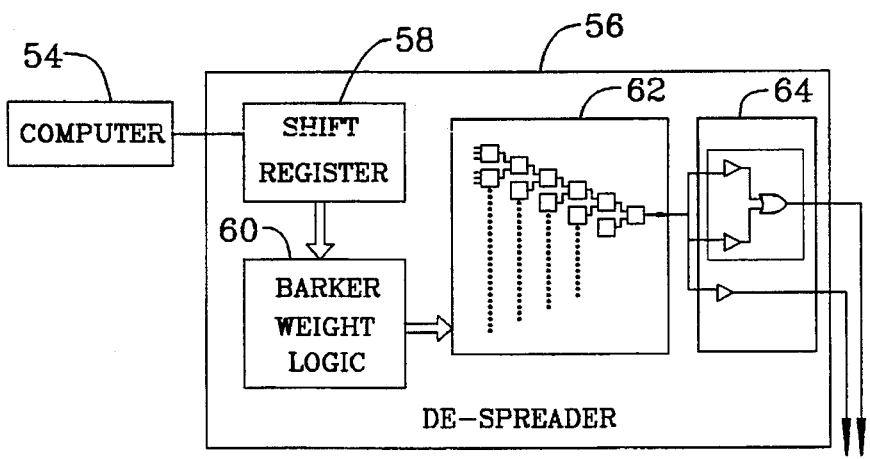
FIG. 5 is a schematic block diagram showing further details of one form of the spread spectrum de-spreader used as part of the preferred form of the present invention.

The de-spreader 56 of this embodiment preferably also includes means for delaying the demodulated signals to create blocks of binary data in each binary data bit as shown in more detail in FIG. 5. Preferably, the delay means includes a shift register 58 for storing the information associated with each block of the 11-bit Barker code. It should be understood that shift register 58 is driven by clock signals having the same frequency as those provided by the above-discussed master clock 46. In practice, the shift register 58 has approximately sixty-six output lines that simultaneously receive data shifted through the shift register 58.

The de-spreader 56 also preferably includes a digital weighting device 60 (i.e., a multiplier) for the individual output lines of the shift register 58. The logic employed by the weighting device 60 can be, for example, an array of invertor gates with one such gate connected to each stage of the shift register 58 which is low (i.e., a binary "0") when the 11-bit Barker code is properly aligned in the shift register 58. As so configured, the weighting device 60 would weight six samples of each Barker chip stored in the shift register 58 using the 11-bit Barker code sequence. Accordingly, if an interference-free binary "1" (represented by the non-inverse Barker code) were provided to the weighting device 60, the device would produce a 66-bit string of ones by inverting the appropriate bits; on the other hand, if an interference-free binary "0" were provided, the device would produce a string of sixty-six binary zeros by inverting the same bits. The de-spreader 56 further includes a plurality of adders 72 and 76 which operate to spread interference signals which may have combined with the data during transmission. This has the effect of substantially reducing the amplitude of the interference signals at any given point of the frequency spectrum. Therefore, the de-spreader 56 basically functions as a matched filter, and the frequency spreading of the interference signals enhances the detection of the data components in the demodulated signals. The output of the de-spreader 56 is received by a data extractor 66 which extracts the data and clock signals from the output of the de-spreader 56. The data extractor 66 generates a received clock signal and a received data signal as well as a carrier detect signal to indicate that a valid signal has been received by the receiver 14. The received data signal and received clock signal are received by a de-scrambler 68 which performs a function which is the inverse of the scrambler 38 in the transmitter 12.

In the preferred form of the present invention, the serial digital data and data clock signals are then output from the de-scrambler 68 of the spread spectrum receiver 14 to the synchronization detector circuit 28 and the data reformatting processor 16.

Figure 6:
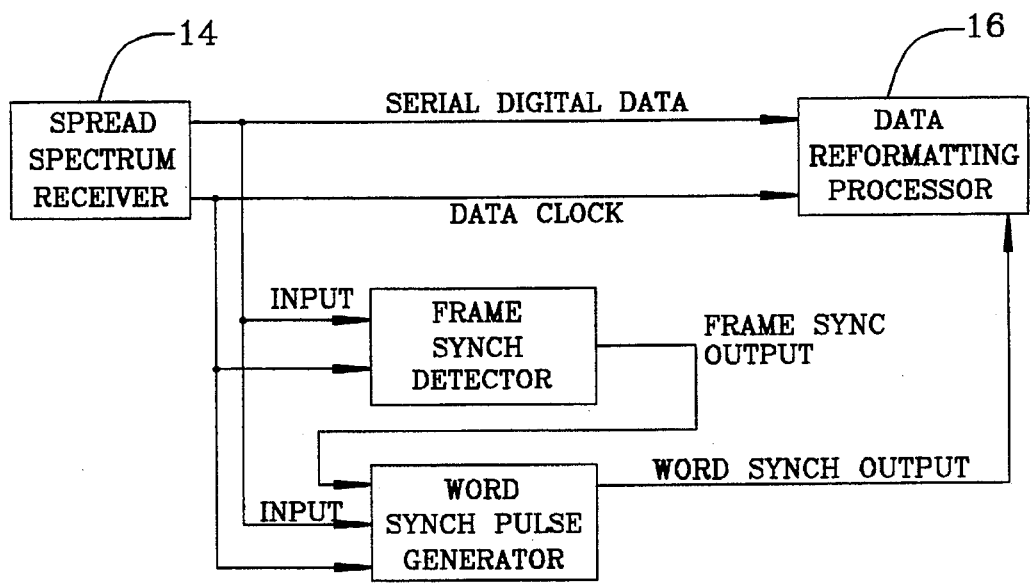
FIG. 6 is a schematic block diagram showing further details of the data synchronization detector circuit of the preferred form of the present invention.
Figure 10:
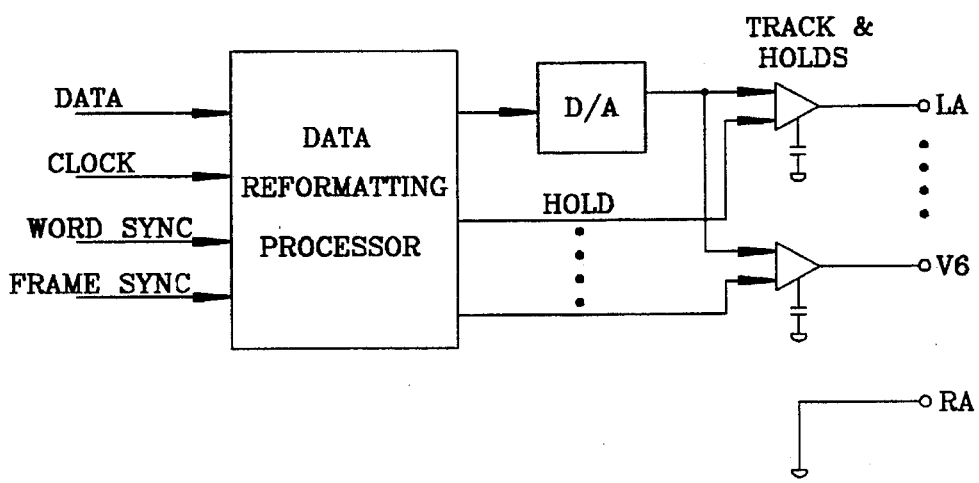
FIG. 10 is a schematic block diagram of an alternate form of a data reformatting processor for use with the preferred form of the present invention.
Figure 7:
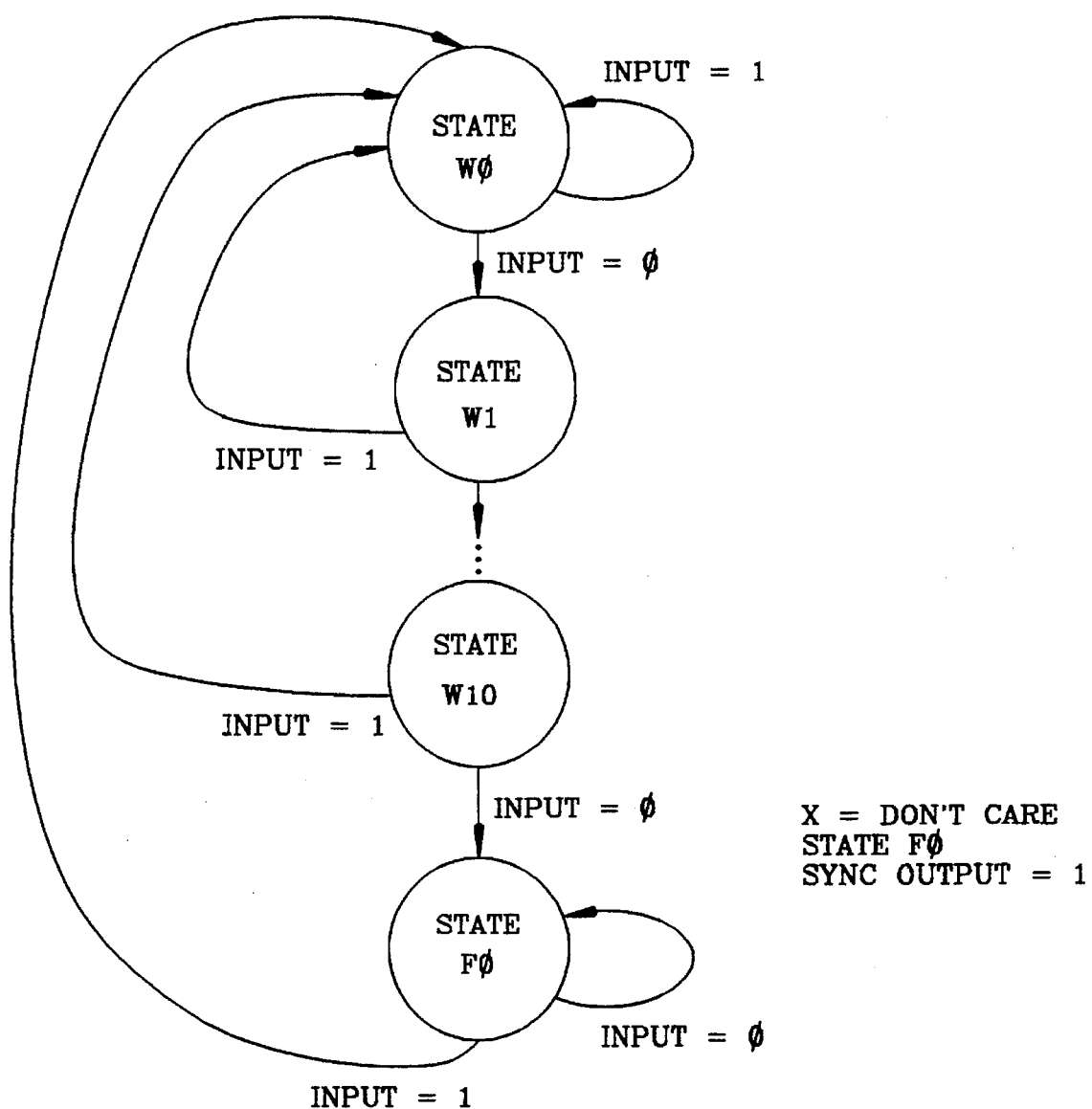
FIG. 7 is a flow chart of the word synchronization detector of the preferred form of the present invention.
Figure 8:
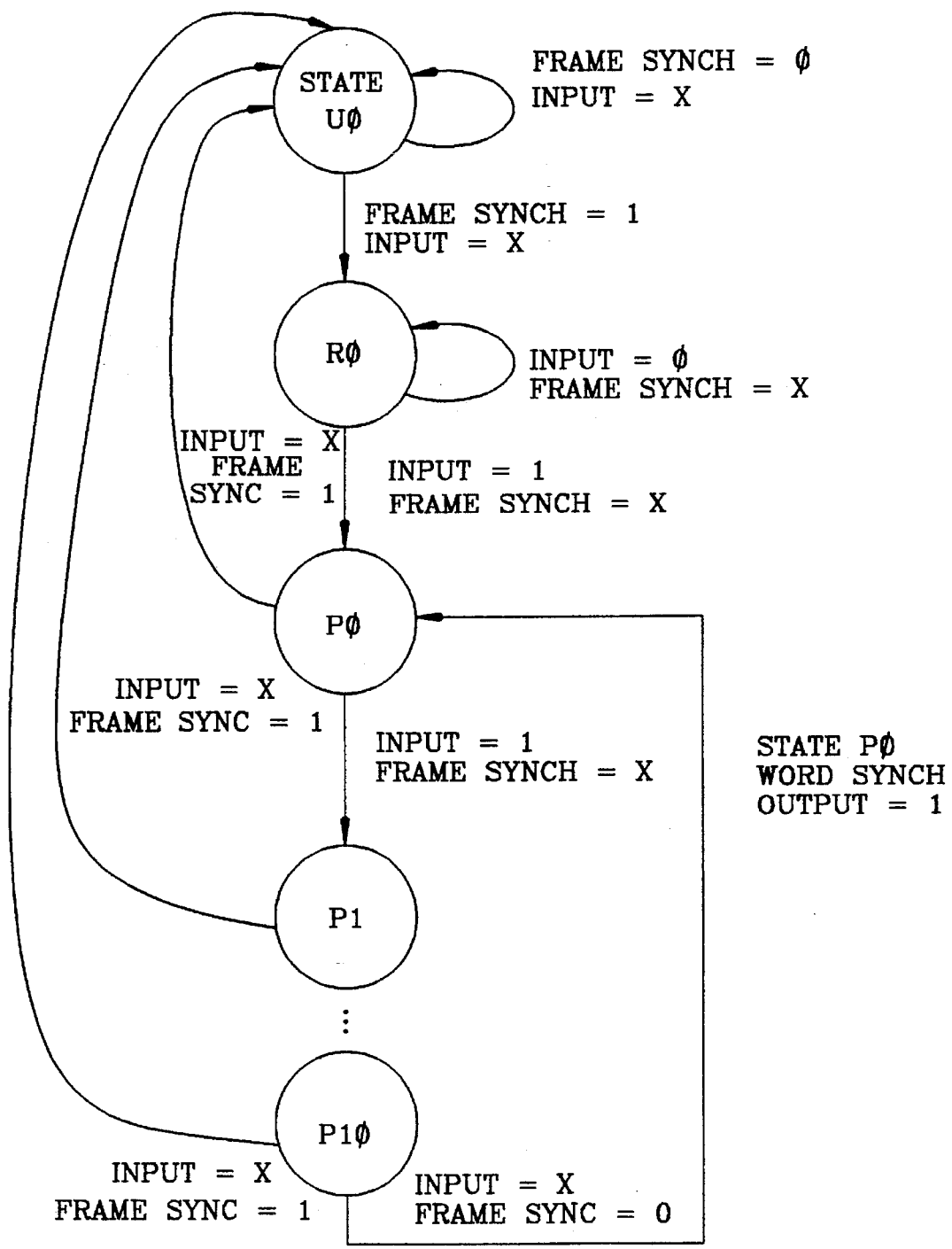
FIG. 8 is a flow chart of the frame synchronization detector of the preferred form of the present invention.
Figure 11:
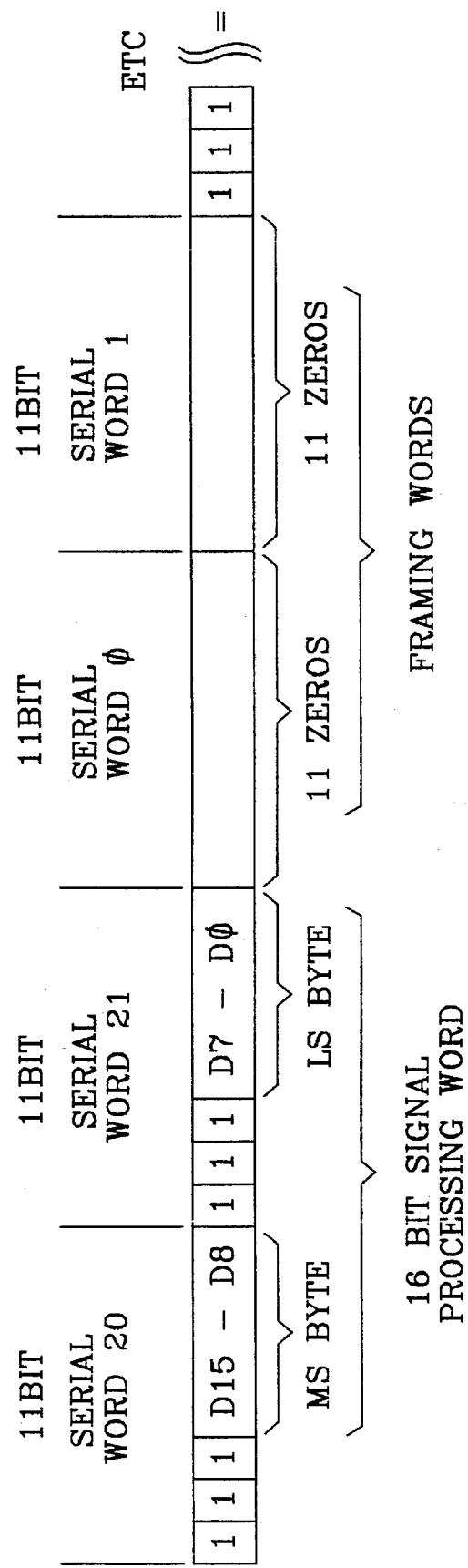
FIG. 11 is illustrative of the format of the data signal provided to the spread spectrum transmitter by the digital signal processor.

As described above, the digital signal processor 26 in this embodiment converts the data from the A to D converter 24 which is organized as eight channels of 8-bit words at a rate of 512,000 bits per second for use by the spread spectrum transmitter 12 and receiver 14. The serial digital data output by the spread spectrum receiver 14 is then received by the data reformatting processor 16 and the synchronization detector circuit 28 as twenty-two 11-bit words at 121K bits per second. The purpose of the synchronization detector circuit 28 as shown in FIG. 6 is to identify the framing words in the data stream, and it is believed that nearly any synchronization detecting mechanism may be used with the present invention. As shown in FIG. 11, the framing order of the data in this embodiment is preferably comprised of two words, each having eleven zeros. Each other data word has eight data bits which are arbitrary and include three least significant bits which are ones padded into the most significant bits of the 11-bit word. As shown in FIG. 6, the frame synchronization detector 70 of the synchronization detector circuit 28 examines the data stream until it finds eleven consecutive bits of zeros. When eleven bits of consecutive zeros are identified, the frame synchronization detector 70 is set to equal "1." The word synchronization detector 72 looks for the frame synchronization detector 70 to equal "1." If the frame synchronization detector 70 equals "1," the word synchronization detector 72 begins counting with the first non-zero data bit and produces the word synchronization pulse every eleven data bits. The word synchronization pulse is transmitted from the synchronization detector circuit 28 to the data reformatting processor 16 and then to the back end 18. FIGS. 7 and 8 represent flow charts of one basic method of determining word and frame synchronization. It is anticipated that other methods may be used with the present invention.

The data reformatting processor 16 receives the serial digital data and the data clock signal from the spread spectrum receiver 14. The serial digital data is preferably received as twenty-two 11-bit words at 121K bits per second and uses the word framing pulses from the synchronization detector circuit 28 to reformat the data to sixteen 16-bit words at 128K bits per second.

As shown in FIG. 9, serial digital data, a 128K bit per second clock signal and the word synchronization signal are received by the back end 18 from the data reformatting processor 16. The data is received by a de-serializer 74 to form electrode difference signals. Examples of typical electrode difference signals are LA-RA; LL-RA; V1-RA; V2-RA; V3-RA; V4-RA; V5-RA and V6-RA. The electrode difference signals are then processed in a lead forming step 76 to recreate the leads as originally received by the front end 10. The recreated leads are then passed through one or more low pass filters 78 to restore the low frequency portion of the signal. The restored signals are then received by a hybrid digital computer 80 which displays, prints and/or analyzes the desired waveforms on a CRT display 82 and/or a chart recorder 84 or other printer.

As described briefly above, FIG. 9 illustrates an alternate form of the present invention. This embodiment is particularly designed for use in systems where it is desirable or necessary for an analog output to be received by the back end 18 rather than the direct digital output disclosed in the preferred form of the present invention. In this embodiment, a digital to analog converter 86 receives the output from the data reformatting processor 16. The analog data stream is then applied to a track and hold system 88 to reproduce signals that are substantially equivalent to the signals that were originally digitized by the front end 10. These signals may then be applied to any ECG device and reproduced as if they were coming directly from the body of the patient. In this embodiment, the differentiation step shown in FIG. 3 is removed so that there is a high pass type of function applied to the signal by the digital signal processor 26.

The foregoing is intended to be illustrative of one basic form of the present invention where a single transmitter transmits to a single receiver. Other configurations are anticipated. For example, a system may be designed where multiple transmitters may be used with individual or multiple receivers where the receiver selects the appropriate transmission by recognizing the appropriate spreading code. Alternately, a system may be designed where different physiological signals are transmitted from a common transmitter to multiple receivers or where multiple pairs of receivers and transmitters are used in the same vicinity. These and other transmitter and receiver combinations are believed to be possible using transmission systems such as time division multiple access systems or code division multiple access systems.

What is claimed is:

1. A spread spectrum telemetry system for the acquisition of physiological signals from a patient and transmission of said signals to a data receiving device, said system comprising;

a first device for the acquisition of the desired physiological data from the patient and for processing a physiological signal consisting of a data stream corresponding thereto;

means for producing a data stream representative of a predetermined code sequence;

said first device further including a spread spectrum signal transmission device which combines said data stream representative of said physiological signal with said data stream representative of a predetermined code sequence to form a combined data transmission signal which is transmitted continuously as a spread spectrum signal from said first device over a wide frequency bandwidth;

a second device including a spread spectrum signal receiving device which receives said spread spectrum signal from said first device;

a demodulation processor associated with said second device which separates said data stream representative of said physiological signal from said data stream representative of a predetermined code sequence and converts said data streams into a serial data stream and a clock signal;

a physiological data receiving device associated with said second device for the receipt and utilization of said data stream representative of said physiological signal; and a synchronization detector in said second device for searching said spread spectrum signal for framing words and said synchronization detector using said framing words to synchronize said spread spectrum signal and allow said data stream representative of said physiological signal to be separated therefrom.

2. The system of claim 1 wherein said spread spectrum signal transmitter transmits said spread spectrum signal from said first device to said second device in a radio frequency range of about 2400 to 2483 MHz.

3. The system of claim 1 wherein said spread spectrum signal transmitter transmits said spread spectrum signal from said first device to said second device in a radio frequency range of about 5700 to 5850 MHz.

4. The system of claim 1 wherein said first device transmits said spread spectrum signal to a plurality of said receiving devices and at least one of said plurality of receiving devices selects the proper spread spectrum signal transmission for receipt thereby by recognizing the a predetermined code sequence in said spread spectrum signal transmission.

5. The system of claim 1 wherein a plurality of physiological signals are transmitted via said spread spectrum signal from said first device to a plurality of said receiving devices.

6. The system of claim 1 wherein a plurality of said first devices transmit said spread spectrum signals to a single one of said receiving devices.

7. The system of claim 1 wherein said acquired physiological signals include signals representative of ECG waveforms therein and said receiving device provides a real time representation of the ECG waveforms of the patient.

8. A method for transmitting physiological signals acquired from a patient by a first device including a transmitter therein to a second device including a data receiving device therein, the method comprising;

acquiring physiological signals from a patient;

processing the acquired physiological signals of the patient to form a digital data stream representative of the physiological signals;

producing a predetermined code sequence;

combining the processed physiological signal with the predetermined code sequence to form a spread spectrum signal;

continuously transmitting the spread spectrum signal from the spread spectrum signal transmitter to the second device which includes a spread spectrum signal receiver associated therewith;

receiving the spread spectrum signal with the receiver of the second device;

separating the processed physiological signal from the predetermined code sequence;

receiving the processed physiological signal;

providing and utilizing the physiological signal for use by a physician with a physiological data receiving device; and transmitting a plurality of physiological signals as part of the spread spectrum signal.

9. The method of claim 8 including the step of transmitting the spread spectrum signal to the receiver of the second device via a frequency hopping system from the first device.

10. The method of claim 8 including the step of transmitting the spread spectrum signal to the receiver of the second device via a pulsed FM modulation system from the first device.

11. The method of claim 8 further including the step of searching the received spread spectrum signal for framing words to determine the synchronization requirements of the spread spectrum signal and to allow the data stream representative of the physiological signal to be separated therefrom.

12. The method of claim 8 including the step of using multiple independent frequency channels for transmitting the spread spectrum signal to the second device.

13. The system of claim 12 including the step of interfacing the received spread spectrum signal synchronously and serially with the receiver of the second device.

14. A spread spectrum telemetry system for transmitting physiological signals acquired from a patient by a first device to a second device including a data receiving device, the system comprising;

means for acquiring physiological signals from a patient;

means for processing said acquired physiological signals of the patient to provide a data stream representative of the acquired physiological signal;

means for providing a predetermined code sequence;

means for combining the processed physiological signal with the predetermined code sequence to form a spread spectrum signal;

means for continuously transmitting said spread spectrum signal including a spread spectrum transmitter for transmitting said spread spectrum signal from said spread spectrum signal transmitter of said first device to a spread spectrum signal receiver of said second device;

means for receiving the spread spectrum signal including said spread spectrum signal receiver as part of said second device;

means for separating and processing said physiological signal from said predetermined code sequence; and means for receiving said processed physiological signal and said means for receiving providing a representation of said physiological signal with a physiological data receiving device.

15. A spread spectrum telemetry system for the acquisition of physiological signals from a patient and transmission of said signals to a data receiving device, said system comprising;

a first device for the acquisition of the desired physiological data from the patient and for processing a physiological signal consisting of a data stream corresponding thereto;

an analog to digital converter to convert said physiological signal representative of said physiological signal into a digital data stream;

a filter to filter said digital data stream;

means for producing a data stream representative of a predetermined code sequence;

said first device further including a spread spectrum signal transmission device which combines said filtered digital data stream with said data stream representative of a predetermined code sequence to form a combined data transmission signal which is transmitted as a spread spectrum signal from said first device;

a second device including a spread spectrum signal receiving device which receives said spread spectrum signal from said first device;

a demodulation processor associated with said second device which separates said filtered digital data stream representative of said physiological signal from said data stream representative of said predetermined code sequence to convert said data streams into a serial data stream representative of said physiological signal; and a physiological data receiving device associated with said second device for the receipt and utilization of said data stream representative of said physiological signal.

16. The system of claim 15 wherein said second device further includes a reformatting processor associated therewith and which converts a serial data stream having a data stream representative of said physiological signal therein to an analog data signal for analysis by said data receiving device.

17. A method for transmitting physiological signals acquired from a patient by a first device including a transmitter therein to a second device including a data receiving device therein, the method comprising;

acquiring physiological signals from a patient;

converting the acquired physiological signals of the patient from an analog signal to a digital data stream with an analog to digital converter to form a digital data stream representative of the physiological signals;

filtering the digital data stream to form a filtered digital data stream;

producing a predetermined code sequence;

combining the filtered digital data stream with the predetermined code sequence to form a spread spectrum signal;

transmitting the spread spectrum signal from the spread spectrum signal transmitter to the second device which includes a spread spectrum signal receiver associated therewith;

receiving the spread spectrum signal with the receiver of the second device;

separating the filtered digital data stream representative of the processed physiological signals from the predetermined code sequence;

receiving and processing the filtered digital data stream to form a processed physiological signal; and providing and utilizing the processed physiological signal for use by a physician with a physiological data receiving device.

18. The method of claim 17 including the step of converting the physiological signal to a digital data stream by an A to D converter in the first device and receiving a reformatted serial data stream with a data reformatting processor in the second device and performing analysis of the processed physiological signal in the second device.

19. A spread spectrum telemetry system for the acquisition, of physiological signals from a patient and transmission of said signals to a data receiving device, said system comprising;

a first device for the acquisition of the desired physiological data from the patient and for processing a physiological signal consisting of a data stream corresponding thereto;

an analog to digital converter to convert said physiological signal representative of said physiological signal into a digital data stream;

means for producing a data stream representative of a predetermined code sequence;

said first device further including a spread spectrum signal transmission device which combines said digital data stream with said data stream representative of a predetermined code sequence to form a combined data transmission signal which is transmitted as a spread spectrum signal from said first device;

a second device including a spread spectrum signal receiving device which receives said spread spectrum signal from said first device;

a demodulation processor associated with said second device which receives said combined data transmission signal and processes said combined data transmission signal to create a processed data stream representative of said physiological signal; and a physiological data receiving device associated with said second device for the receipt and analysis of said processed data stream representative of said physiological signal.

20. The system of claim 19 wherein said first device includes a filter means to filter said digital data stream prior to transmission thereof and said second device further includes a reformatting processor associated therewith and which converts a serial data stream receiving from said demodulation processor having a representation of said physiological signal therein to an analog data signal for analysis by said data receiving device.

21. A method for transmitting physiological signals acquired from a patient by a first device including a transmitter therein to a second device including a data receiving device therein, the method comprising;

acquiring physiological signals from a patient;

converting the acquired physiological signals of the patient from an analog signal to a digital data stream with an analog to digital converter to form a digital data stream representative of the physiological signals;

producing a predetermined code sequence;

combining the digital data stream with the predetermined code sequence to form a spread spectrum signal;

transmitting the spread spectrum signal from the spread spectrum signal transmitter to the second device which includes a spread spectrum signal receiver associated therewith;

receiving the spread spectrum signal with the receiver of the second device;

separating the received spread spectrum signal into a processed physiological signal and a predetermined code sequence;

receiving the processed physiological signal; and analyzing and providing the processed physiological signal for use by a physician with a physiological data receiving and analysis device.

22. The method of claim 21 including the step of converting the physiological signal to a digital data stream by an A to D converter in the first device and receipt of a reformatted serial data stream from a data reformatting processor in the second device and performing analysis of the reformatted serial data stream received from the data reformatting processor in the second device.

23. A spread spectrum telemetry system for transmitting physiological signals acquired from a patient by a first device to a second device including a data receiving device, the system comprising;

means for acquiring physiological signals from a patient;

means for converting said acquired physiological signals of the patient from an analog signal to a digital data stream to provide a digital data stream representative of the acquired physiological signal;

means for filtering said digital data stream;

means for creating a predetermined code sequence;

means for combining the filtered digital data stream with said predetermined code sequence to form a spread spectrum signal;

means for transmitting said spread spectrum signal including a spread spectrum transmitter for transmitting said spread spectrum signal from said spread spectrum signal transmitter of said first device to a spread spectrum signal receiver of said second device;

means for receiving the spread spectrum signal including said spread spectrum signal receiver as part of said second device;

means for separating and processing said physiological signal from said predetermined code sequence; and means for receiving said processed physiological signal and said means for receiving providing a representation of said physiological signal with a physiological data receiving device.

24. A spread spectrum telemetry system for transmitting physiological signals acquired from a patient by a first device to a second device including a data receiving device, the system comprising;

means for acquiring physiological signals from a patient;

means for converting said acquired physiological signals of the patient from an analog signal to a digital data stream provide a digital data stream representative of the acquired physiological signal;

means for creating a predetermined code sequence;

means for combining said digital data stream with said predetermined code sequence to form a spread spectrum signal;

means for transmitting said spread spectrum signal including a spread spectrum transmitter for transmitting said spread spectrum signal from said spread spectrum signal transmitter of said first device to a spread spectrum signal receiver of said second device;

means for receiving the spread spectrum signal including said spread spectrum signal receiver as part of said second device;

means for separating and processing said physiological signal from said predetermined code sequence;

means for receiving said processed physiological signal including means for receiving and providing a representation of said physiological signal with a physiological data receiving device;

means for performing an analysis of said representation of said physiological signal for use by a physician.

* * * * *